ns Patent [19]

Hauck et al.

[11] 4,022,788
[45] May 10, 1977

[54] INDANE TETROL AMINES

[75] Inventors: Frederic Peter Hauck, Somerville; Joyce Reid, Highland Park; Vinayak V. Kane, Princeton, all of N.J.

[73] Assignee: E. R. Squibb & Sons, Inc., Princeton, N.J.

[22] Filed: Apr. 23, 1975

[21] Appl. No.: 570,911

Related U.S. Application Data

[63] Continuation-in-part of Ser. No. 467,033, May 6, 1974, abandoned.

[52] U.S. Cl. .................. 260/293.56; 260/268 BC; 260/326.5 C; 260/326.33; 260/563 C; 260/563 P; 260/563 R; 260/570.9; 424/250; 424/267; 424/274

[51] Int. Cl.² ............. C07D 211/06; C07D 295/08; C07D 295/10

[58] Field of Search ............. 260/268 BC, 326.5 C, 260/326.33, 293.56, 570.9, 563 C, 563 R, 563 P; 424/250, 267, 274

[56] References Cited
OTHER PUBLICATIONS

V. P. Arya et al., *J. of Pharmaceutical Sciences*, vol. 58, pp. 432–440 (1969).
Prabhash Chandra Das et al., *J. of Medicinal Chemistry*, vol. 14, No. 9, pp. 890–891.

*Primary Examiner*—Donald G. Daus
*Assistant Examiner*—Jose Tovar
*Attorney, Agent, or Firm*—Lawrence S. Levinson; Merle J. Smith; Burton Rodney

[57] ABSTRACT

The compounds of the invention have the formula

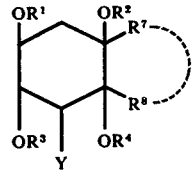

wherein
Y is a radical of the formula

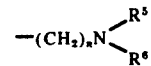

or of the formula

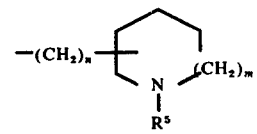

wherein $(CH_2)$ is a straight or branched chain alkyl radical, $n$ is 1–6, $m$ is 0 or 1 and $R^5$ and $R^6$ may be the same or different and may be hydrogen, alkyl, arylalkyl, and $R^5$ and $R^6$ together with the nitrogen to which they are attached may be pyrrolidino, piperadino or N'-alkyl piperazino;
$R^1$, $R^2$, $R^3$ or $R^4$ may be the same or different and may be hydrogen; alkyl, trifluoromethyl; alkanoyl; haloalkanoyl; alkoxycarbonyl of the formula

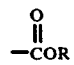

wherein R is an alkyl radical; alkoxyalkyl; aminoalkanoyl of the formula

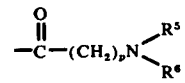

wherein $R^5$ and $R^6$ are as previously defined and $p$ is 0–3; 2-, 3-, or 4-pyridylcarbonyl; phenyl; monosubstituted phenyl wherein the substituent is alkyl, alkoxy, hydroxy, nitro, amino, or dialkylamino; alkenoyl; or aroyl;
$R^7$ and $R^8$ may be the same or different and may be hydrogen or alkyl, and $R^7$ and $R^8$ taken together with the carbon atoms bearing substituents $OR^2$ and $OR^4$ may form a cycloalkyl ring. These compounds have been found useful in the treatment of hypertension in mammalian species, e.g., rats, as surface active agents, as in vitro antibacterial compounds and as water softeners.

5 Claims, No Drawings

INDANE TETROL AMINES

REFERENCE TO OTHER APPLICATION

This application is a continuation-in-part of copending application Ser. No. 467,033 filed May 6, 1974, now abandoned.

BACKGROUND OF THE INVENTION

The problem of hypertension is widely prevalent and while some progress has been made in its treatment, there is a need for more effective compounds, and for compounds which have fewer side effects.

OBJECTS OF THE INVENTION

It is an object of the present invention to provide new compounds which are effective in treating hypertension. A further object is to provide methods for the preparation of these compounds. Another object is to provide pharmaceutically acceptable compositions incorporating the compounds of the present invention. Still another object is to provide methods for the therapeutic administration of the compounds of the present invention. These and other objects of the present invention will be apparent from the following description.

SUMMARY OF THE INVENTION

The compounds of the invention have the formula

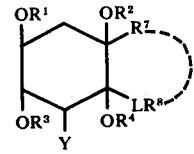

I wherein
Y is a radical of the formula

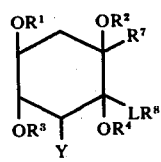

I or of the formula

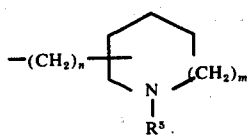

wherein (CH$_2$) is a straight or branched chain alkyl radical, $n$ is 1–6, $m$ is 0 or 1 and R$^5$ and R$^6$ may be the same or different and may be hydrogen, alkyl of from 1 to 3 carbon atoms, arylalkyl and R$^5$ and R$^6$ together with the nitrogen atom to which they are attached may be pyrrolidino, piperidino of N'-alkyl piperazin- wherein the alkyl radical has from 1 to 3 carbon atoms;

R$^1$, R$^2$, R$^3$ or R$^4$ may be the same or different and may be hydrogen; alkyl of from 1 to 4 carbon atoms; alkanoyl of from 1 to 4 carbon atoms, haloalkanoyl of from 1 to 4 carbons wherein the halogen may be F, Cl, Br or I; alkoxycarbonyl of the formula

wherein R is an alkyl radical of from 1 to 4 carbon atoms; alkoxyalkyl or benzyloxyalkyl wherein the alkoxy radical has from 1 to 3 carbons and the alkyl radical has from 1 to 3 carbons; aminoalkanoyl of the formula

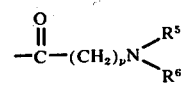

wherein R$^5$ and R$^6$ are as previously defined and $p$ is 0–3; 2—3—, or 4-pyridylcarbonyl; phenyl; monosubstituted phenyl wherein the substituent is alkyl of from 1 to 4 carbons, alkoxy of from 1 to 4 carbons, hydroxy, nitro, amino, or dialkylamino wherein each alkyl radical may have from 1 to 4 carbon atoms; or alkenoyl of 3 or 4 carbon atoms; or aroyl of the formula

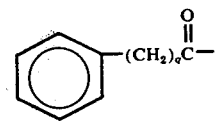

wherein $q$ is 0–3;
R$^7$ and R$^8$ may be the same or different and may be hydrogen or alkyl of from 1 to 4 carbons, and R$^7$ and R$^8$ taken together with the carbon atoms bearing substituents OR$^2$ and OR$^4$ may form a cycloalkyl ring having from 5 to 7 carbon atoms. These compounds have been found useful in the treatment of hypertension in mammalian species, as surface active agents, as in vitro anti-bacterial compounds and as water softeners.

DETAILED DESCRIPTION

The present invention relates to cyclohexane tetrol derivatives which have a lowering effect on blood pressure and are useful in the treatment of hypertension in mammalian species, for example, genetically hypertensive rats. In addition, the compounds of the invention are surface active agents, have anti-bacterial properties in vitro and are also useful as water softeners. A compound of the invention as well as its physiologically acceptable acid addition salts may be compounded according to conventional pharmaceutical practice or oral or parenteral dosage forms such as tablets, capsules, elixirs, injectables or powders for administration in dosage levels of from about 25 mg to about 100 mg per day, preferably from about 25 mg to about 50 mg per day, in a single dose or in from 2 to 4 divided doses.

The compounds of the present invention have the general formula

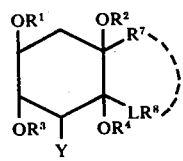

I

In the foregoing formula Y may be a radical of the formula

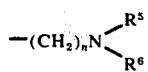

or of the formula

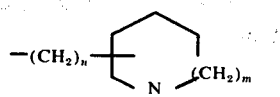

wherein (CH₂) is a straight or branched chain alkyl radical, n is 1 to 6, m is 0 or 1 and R⁵ and R⁶ are as previously defined. Examples of specific radicals for Y are the following:

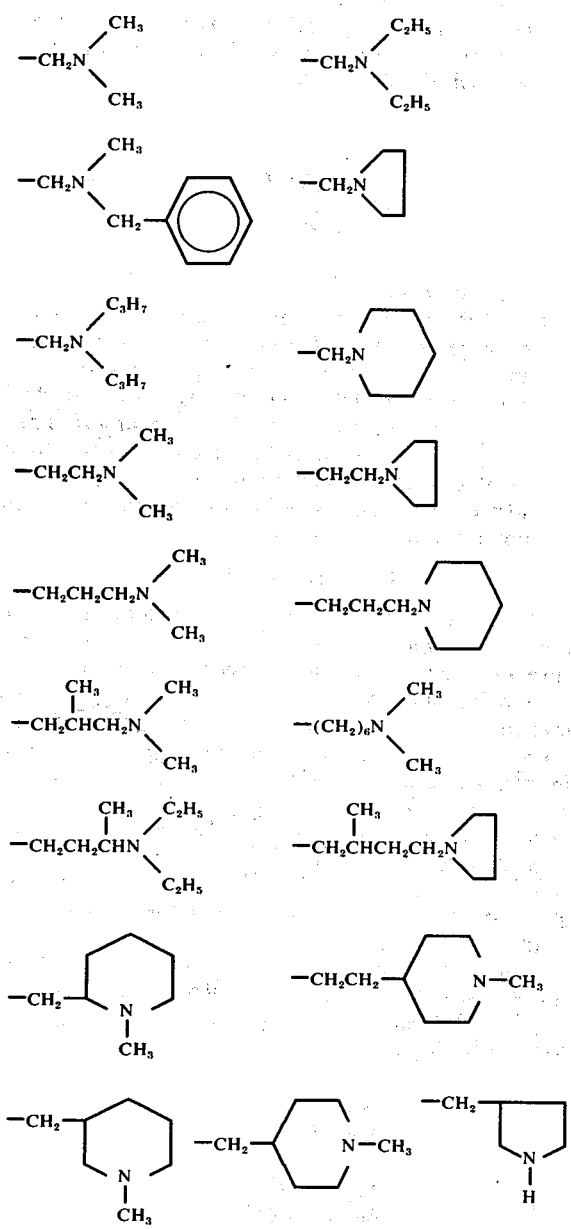

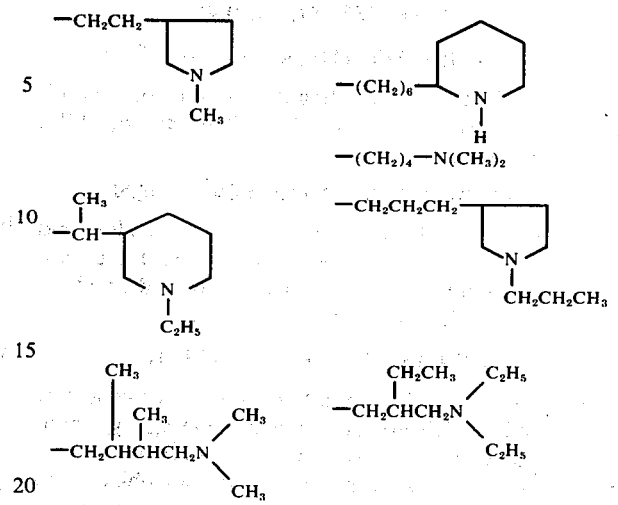

In the foregoing formula, $R^1$, $R^2$, $R^3$ and $R^4$ may be the same or different. Examples of specific radicals for each of $R^1$, $R^2$, $R^3$ and $R^4$ are the following: hydrogen; methyl, ethyl, n-propyl, i-propyl, n-butyl, i-butyl or t-butyl; trifluoromethyl; formyl, acetyl, propionyl, isopropionyl, butanoyl, isobutanoyl, or t-butanoyl; chloroacetyl, bromoacetyl, trifluoroacetyl, 2-bromopropionyl, 3-bromopropionyl, 2-chloropropionyl, 3-chloropropionyl, 2,3-dibromopropionyl, or 2,3-dichlorobutanoyl; methoxycarbonyl, ethoxycarbonyl, propoxycarbonyl, isopropoxycarbonyl, butoxycarbonyl, isobutoxycarbonyl or t-butoxycarbonyl; methoxyethyl, methoxypropyl methoxymethyl, ethoxymethyl, ethoxyethyl, ethoxypropyl, propoxymethyl, propoxyethyl, propoxypropyl, i-propoxymethyl, i-propoxyethyl, i-propoxypropyl, methoxyisopropyl, ethoxyisopropyl, propoxyisopropyl; amido, dimethylamido, diethylamido, dipropylamido, diisopropylamido, pyrrollidinocarbonyl, piperidinocarbonyl; 2-aminoacetyl, 3-aminopropionyl, 4-aminobutanoyl, dimethylaminoacetyl, diethylaminopropionyl, dimethylaminobutanoyl, diisopropylaminoacetyl; 2-, 3- or 4-pyridylcarbonyl; phenyl, o-tolyl, m-tolyl, p-tolyl, o-ethylphenyl, m-propylphenyl, p-butylphenyl; o-hydroxyphenyl, m-methoxyphenyl, p-ethoxyphenyl; o-nitrophenyl, m-nitrophenyl, p-aminophenyl; p-dimethylaminophenyl; o-allylphenyl or m-crotonylphenyl;

$R^7$ and $R^8$ may be hydrogen, methyl, ethyl, propyl i-propyl, butyl, sec-butyl, t-butyl or together may be

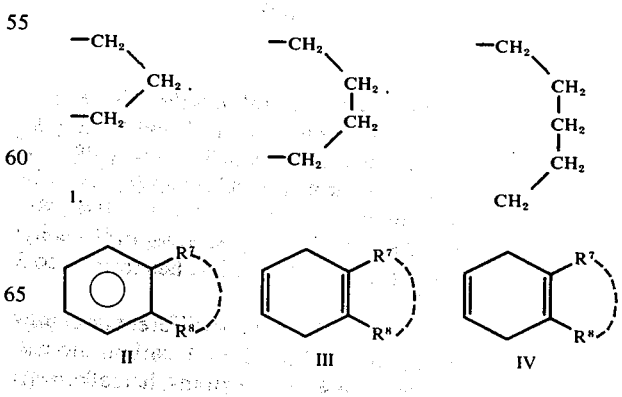

-continued

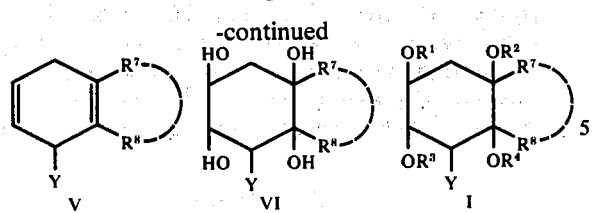

A compound of formula II wherein $R^7$ and $R^8$ are as previously defined is converted by means of a Birch reduction under conventional conditions, e.g., by reaction with lithium in the presence of liquid ammonia, and a proton source such as a lower alkanol and a cosolvent such as ethyl ether, to yield a compound of formula III. The latter upon treatment with $NaNH_2$ in refluxing $NH_3$ forms an anion of formula IV, which is in turn converted to a compound of formula V by treatment in refluxing $NH_3$ with a halide of formula X-Y wherein X is Cl or Br, preferably Cl. A compound of formula V is treated with excess $H_2O_2$ and formic acid at about room temperature with cooling. After completion of the reaction the mixture is rendered alkaline by treating with a base. The so-prepared tetrol of formula VI is converted to the final compound of formula I by treatment with the appropriate esterifying agent in the presence of an acidic catalyst such as $HClO_4$, with cooling.

2.

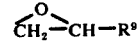

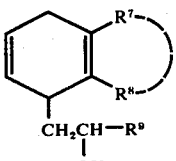

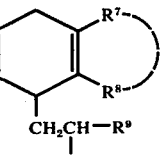

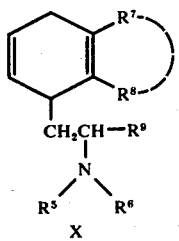

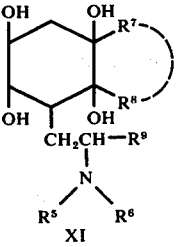

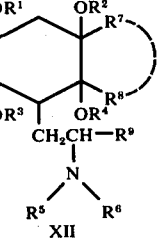

An alternate procedure is to react a compound of formula IV with an epoxide of formula VII in the presence of an alkali metal amide in refluxing ammonia to yield a compound of formula VIII. In the compound of formula VII, $R^9$ is alkyl of from 1 to 4 carbons, phenyl, H, alkyl of 1-4 carbons substituted by phenyl or phenoxy or by a substituted phenyl or phenoxy radical wherein the substituent is halogen, amino, alkyl of 1 to 4 carbons, alkoxy of 1 to 4 carbons or dialkyl amino wherein each alkyl radical is from 1 to 4 carbon atoms. The compound of formula VIII is then converted to the halide of formula IX wherein X is chlorine or bromine and the latter compound in turn is converted to the compound of formula X by conventional techniques. The compounds of formula X is then converted to the tetrol of formula XI and the latter to the compound of formula XII under the same conditions respectively as employed in proceeding from compound V to VI to I.

Alternatively, a solution of substituted cyclohexadiene of formula V is dissolved in a carboxylic acid and treated in the cold portionwise with about 1 equivalent of a strong acid with a non-participating anion, i.e., one which does not open an epoxide, e.g., perchloric, sulfuric or nitric. The resulting solution of the salt is treated at temperatures of from about 10° to about 20° with at least about 2 equivalents of peracid corresponding to the carboxylic acid employed at temperatures of up to about 35°–40°. The mixture is stirred at from about 30° to about 55° for several hours, then cooled in ice and slowly diluted with ether to precipitate the salt of the partially acylated tetrol as an oil product. The product of formula I is washed with ether, cooled in a dry ice-acetone bath to about −30° and treated with the appropriate acid anhydride followed by a small amount of a strong acid, e.g., perchloric, sulfuric or paratoluenesulphonic. After about 1 hour at a temperature of from about −30° to about −15°, the mixture is held overnight at a temperature of from about −15° to about 0°. Excess acylating agent is then destroyed at temperatures of from about −10° to about 0° by addition of excess methanol. The mixture is then poured into cold concentrated ammonia and the product extracted into dichloromethane, treated and freed of solvent. The product is then purified by recrystallization or chromatography.

The compounds of the present invention include the stereoisomers, optical isomers and conformers having the structural formula I. The compounds of the present invention have a lowering effect on blood pressure and are useful in the treatment of hypertension in mammalian species, e.g., dogs and rats. In addition to the compounds of the present invention are useful surface active agents, as in vitro antibacterial compounds and as water softeners. A compound of formula I as well as its physiologically acceptable salts may be compounded according to pharmaceutical practice in oral or parenteral dosage form such as tablets, capsules, elixirs, injectables or powders for administration in quantities of from about 10 mg to about 400 mg per day, preferably from about 50 mg to about 200 mg per day, in 1 dose or from 2 to 4 divided doses.

The following examples illustrate the present invention without, however, limiting the same thereto. All temperatures are expressed in degrees Centigrade.

EXAMPLE 1

3a, 7a-trans-5,6-trans-Hexahydro-4-(3-piperidinopropyl)-3a, 5,6,7a-indantetrol

To a suspension of 1.0 mole of $NaNH_2$ in 1 liter liquid $NH_3$ there is added 60 g (0.50 mole) of 4,7-dihydroindan in 125 ml ether. After 15 minutes stirring, the mixture is treated portionwise with solid N-bromopropylpiperidine hydrobromide at a rate slow enough to ensure the return of a slight yellow color to the mixture between spatulafuls. After addition is completed, stirring is continued 1 hour before the addition of 500 ml of ether and quenching with solid $NH_4Cl$ as rapidly as possible. After $NH_3$ has evaporated, solids are removed by filtration and solvents and starting material removed ultimately by means of an oil pump. There is thus obtained 52 g (82%) of aminoalkyl diene whose vapor phase chromatography indicates a mixture of 80% desired isomer contaminated with 20% of a second isomer but no bisalkylation product.

The above 52 g is dissolved in 500 ml of cold 88% formic acid and treated in 3 portions over 2 hours with 150 ml 30% $H_2O_2$ at 15°–20°. After stirring overnight in a bath of water, the mixture is freed of solvent at the pump, and the residue taken up in 250 ml ethanol and hydrolyzed by the addition of 75 ml 50% NaOH. The temperature is allowed to rise to 65° and stirring continued for 1 hour. The mixture is poured into water and the product extracted into ether. After drying and solvent removal, the residue (36 g) is taken up in ethyl acetate and left to stand. A 25 g first crop is deposited. A sample recrystallized from isopropanol-ether has mp 191°–200°.

EXAMPLE 2

3a,7a-trans-5,6-trans-Hexahydro-4-(3-piperidinopropyl)-3a,5,6,7a-indantetrol, tetraacetate ester 3a,7a-trans-5,6-trans-Hexahydro-4-(3-piperidinopropyl)-3a,5,6,7a-indantetrol, (1.4 g, 0.0046 M), prepared as described in example 1 is dissolved in 30 ml acetic anhydride and 1.5 ml glacial acetic acid. The solution is cooled to −30° and perchloric acid (3.0 ml of 70%) is added dropwise over a period of 20 minutes. After standing at −15° for 20 hours, the mixture is again cooled to −30° and methanol (15 ml) is added dropwise over a period of 30 minutes. The mixture is then poured into 60 ml cold concentrated $NH_4OH$. The product is extracted into chloroform and the chloroform solution is dried. The solvent is removed in vacuo leaving tan crystalline material. This material is recrystallized from hexane to yield the title compound, mp 107°–110° C.

EXAMPLE 3

3a,7a-trans-5,6-trans-1-Hexahydro-4-(3-piperidinopropyl)-3a,5,6,7a-indantetrol, tetraacetate ester A solution of 0.1 mole of aminoalkyl diene prepared as described in paragraph 1 of example 1 in 144 ml of glacial acetic acid at 5° C is treated in three portions over 5 minutes with 15 g (0.105 mole) of 70% perchloric acid. To the solution of perchlorate at 15° C is added 47.7 g (0.25 mole) of 40% peracetic acid over 10 minutes maintaining the temperature at 35° C with an ice bath. After the addition is complete the bath is removed and the mixture maintained at 32° C temperature for 1 hour, then is heated at 40°–55° C for 2 hours. The heat is removed and replaced by an ice bath. When cold (5° C) the mixture is slowly diluted with 700 ml of ether, the oil allowed to settle, and the supernatant solution decanted. The oil is washed with 2 × 300 ml portions of ether, then covered with a blanket of nitrogen and cooled in a dry ice-acetone bath to −30° C. To this is added 250 ml of cold (5° C) acetic anhydride, followed by 2 ml of 70% perchloric acid. The mixture is stirred for 1 hour at −30° to 0° to dissolve all the oil, then cooled at −15° C overnight without stirring.

The stirred mixture in an ice-acetone bath at −10° C is treated with 120 ml of methanol at a rate to maintain the temperature at 10° C. After 30 minutes the temperature drops sharply as the last of the excess anhydride is consumed, and the mixture is poured into 500 ml of concentrated ammonium hydroxide cooled in an ice bath. This is then extracted with dichloromethane (1 l.), dried for 1 hour over magnesium sulfate, filtered and evaporated completely to a tan solid. Hexane (400 ml) is added and boiled and the solid is filtered, washed with hexane, and dried in air to give 20 g of solid. The hexane filtrates deposit another 1.3 g of crystalline solid.

The solids are combined and taken up in 500 ml of hot ethyl acetate cooled to 25° C and suction filtered through a dry pad of 350 g of Woelm neutral alumina, activity II, layered over with Celite. The filter cake is washed with another 500 ml of ethyl acetate and the resulting solid swirled with 300 ml hexane, filtered and dried to give the tetraacetate product, m.p. 107°–110° C.

EXAMPLE 4

3a,7a,-trans-5,6-trans-Hexahydro-4-[4-(dimethylamino)-butyl]-3a,5,6,7a-indanetetrol Following the procedure of example 1 but substituting for N-bromopropylpiperidine hydrobromide an equivalent amount of dimethylaminobutyl chloride hydrochloride, the title compound is obtained.

EXAMPLE 5

3a,7a-trans-5,6-trans-Hexahydro-4-[3-(dimethylamino)-propyl]-3a,5,6,7a-indanetetrol Following the procedure of example 1 but substituting for N-bromopropylpiperidine hydrobromide an equivalent amount of dimethylaminopropyl chloride hydrochloride, the title compound is obtained, mp 138°–139° C.

EXAMPLE 6

3a,7a-trans-5,6-trans-Hexahydro-4-[3-(diethylamino)ethyl]-3a,5,6,7a-indanetetrol Following the procedure of example 1 but substituting for N-bromopropylpiperidine hydrobromide an equivalent amount of diethylaminoethyl chloride hydrochloride, the title compound is obtained.

EXAMPLE 7

3a,7a-trans-5,6-trans-Hexahydro-4-[(4-methyl-1-piperazinyl)-methyl]-3a,5,6,7a-indanetetrol Following the procedure of example 1 but substituting for N-bromopropylpiperidine hydrobromide an equivalent amount of 1-chloromethyl-4-methylpiperazine, the title compound is obtained.

EXAMPLE 8

3a,7a-trans-5,6-trans-Hexahydro-4-[(1-methyl-4-piperidyl)-methyl]-3a,5,6,7a-indanetetrol Following the procedure of example 1 but substituting for N-bromopropylpiperidine hydrobromide an equivalent amount of N-methyl-4-chloromethylpiperidine hydrochloride, the title compound is obtained.

EXAMPLE 9

3a,7a-trans-5,6-trans-Hexahydro-4-[2-(1-methyl-4-piperidyl)-ethyl]-3a,5,6,7a-indanetetrol Following the procedure of example 1 but substituting for N-bromopropylpiperidine hydrobromide an equivalent amount of N-methyl-4-chloroethylpiperidine hydrochloride, the title compound is obtained.

EXAMPLE 10

3a,7a-trans-5,6-trans-Hexadhydro-4-[3-(diethylamino)propyl]-3a,5,6,7a-indanetetrol Following the procedure of example 1 but substituting for N-bromopropylpiperidine hydrobromide an equivalent amount of diethylaminopropyl chloride, the title compound is obtained.

EXAMPLE 11

3a,7a-trans-5,6-trans-Hexahydro-4-[(1-methyl-3-pyrrolidinyl)-methyl]-3a,5,6,7a-indanetetrol Following the procedure of example 1 but substituting for N-bromopropylpiperidine hydrobromide an equivalent amount of 1-methyl-3-chloromethylpyrrolidine, the title compound is obtained.

EXAMPLE 12

3a,7a-trans-5,6-trans-Hexahydro-4-(piperidinyl)methyl-3a,5,6,7a-indanetetrol

Following the procedure of example 1 but substituting for N-bromopropylpiperidine hydrobromide an equivalent amount of 4-chloromethylpiperidine, the title compound is obtained.

EXAMPLE 13

3a,7a-trans-5,6-trans-Hexahydro-4-[β-(1-methyl-piperidyl-2)ethyl]-3a,5,6,7a-indanetetrol Following the procedure of example 1 but substituting for N-bromopropylpiperidine hydrobromide an equivalent amount of 1-methyl-2-(β-chloroethyl)-piperidine, the title compound is obtained.

EXAMPLE 14

3a,7a-trans-5,6-trans-Hexahydro-4-[(1-methyl-2-pyrrolidinyl)-ethyl]-3a,5,6,7a-indanetetrol Following the procedure of example 1 but substituting for N-bromopropylpiperidine hydrobromide an equivalent amount of 1-methyl-2-(β-chloro-ethylpyrrolidine, the title compound is obtained.

EXAMPLES 15 – 24

Treating the tetrols of examples 4–14, respectively, according to the procedure of example 2 but substituting for acetic anhydride and glacial acetic acid an equivalent amount of the anhydride listed in column I below, there is obtained the corresponding tetraester wherein each of $R^1$, $R^2$, $R^3$ and $R^4$ is the radical shown in column II below:

| Starting Material Tertol of example | I anhydride | II $R^{1-4}$ |
|---|---|---|
| 15. | 4 | propionic | propionyl |
| 16. | 5 | trifluoroacetic | trifluoroacetyl |
| 17. | 6 | dichloroacetic | dichloroacetyl |
| 18. | 7 | monochloroacetic | monochloroacetyl |
| 19. | 8 | monobromoacetic | monobromoacetyl |
| 20. | 9 | β-iodopropionic | β-iodopropionyl |
| 21. | 10 | β-methoxypropionic | β-methoxypropionyl |
| 22. | 11 | benzyloxyacetic | benzyloxyacetyl |
| 23. | 12 | N-methylpiperazinoacetic | N-methylpiperazinoacetyl |
| 24. | 13 | N-methylpyrrolidinoacetic | N-methylpyrrolidinoacetyl |

EXAMPLE 25

3a,7a-trans-5,6-trans-Hexahydro-4-(3-piperidinopropyl)-3a,5,6,7a-indantetrol, tetrabenzoate ester The product of example 1 (0.01 mole) is dissolved in pyridine (25 ml) and 2.2 equivalents of benzoyl chloride are added. The mixture is stirred at room temperature for 3 hours, then diluted with water, extracted into ether and dried to yield the title compound.

EXAMPLES 26 – 32

Following the procedure of example 25 but substituting for benzoyl chloride the compound listed in column I, there is obtained the corresponding tetraester wherein each of $R^1$, $R^2$, $R^3$ and $R^4$ is the radical shown in column II:

| | Starting Material: Tertol of example | I | II |
|---|---|---|---|
| 26. | 1 | acryloyl chloride | acryloate |
| 27. | 1 | crotonoyl chloride | crotonoyl |
| 28. | 1 | hydrocinnamoyl anhydride | hydrocinnamoyl |
| 29. | 4 | phenacetyl chloride | phenacetoyl |
| 30. | 5 | nicotinic anhydride | nicotinoyl |
| 31. | 6 | isonicotinic anhydride | isonicotinoyl |
| 32. | 6 | picolinic anhydride | picolinoyl |

EXAMPLE 33

3a,7a:5,6-trans-4-[3-(Dimethylamino)propyl]-hexahydro-1H-indene-3a,5,6,7a-tetrol, tetraacetate ester A 4.1 g sample of the product of example 5 (0.015 mole) in 125 ml of acetic anhydride is cooled to −78° C and treated with 2.260 g (0.016 moles) of 70% perchloric acid. The slurry is allowed to warm to −20°. After standing at −20° for 20 hours, the mixture is again cooled to −78° and 70 ml of methanol is added dropwise over a period of 30 minutes. The mixture is then poured into 150 ml cold concentrated aqueous ammonia. The product is extracted into chloroform and the chloroform solution is dried. The solvent is removed in vacuo leaving tan crystalline material 6.3 g. This is recrystallized from ethyl acetate-hexane to give 3.1 g of analytical sample of 3a,7a:5,6-trans-4-[3-(dimethylamino)-propyl]hexahydro-1H-indene-3a,5,6,7a-tetrol, tetraacetate ester, mp 73°–74° C.

EXAMPLE 34

1,2:4,5-trans-3-[3-(Dimethylamino)propyl]-1,2-dimethyl-1,2,4,5-cyclohexanetetrol, tetraacetate ester To a suspension of 1.0 mole of sodium amide in 1 liter liquid ammonia is added 67.6 g (0.5 moles, 80% purity), 1,2-dimethyl-1,4-cyclohexadiene in 125 ml of ether. After 15 minutes of stirring, the mixture is treated portionwise with 62 g (0.5 moles) of dimethylaminopropyl chloride in 125 ml of ether. After addition is completed stirring is continued for 1 hr, before the addition of 500 ml of ether and quenching with solid ammonium chloride as rapidly as possible. After ammonia has evaporated solids are removed by filtration and solvents removed in vacuo to give 60 g of liquid. This liquid on acid base extraction gives 40 g of the alkylated dienes. This liquid is distilled at the oil pump to give 26.8 g of the monoaminoalkyl diene bp 62–64°/0.05 mm and 10.8 g of bis-alkylation product, bp 110°/0.05 mm.

An amount of 19.3 g (0.1 mol) of N,N,2,3-tetramethyl-2,5-cyclohexadiene-1-propanamine is dissolved in 200 ml of cold 88% formic acid, and treated over a period of 15 minutes with 24.1 ml of 30% hydrogen peroxide (0.280 moles). The temperature rises from 20° to 48° during the next 20 minutes. A cold bath is applied for a few minutes to maintain temperature between 48°–42°. The bath is removed and the temperature drops from 42° to 30° in the next 60 minutes, the solution is left stirring overnight at room temperature. The solution is diluted with 200 ml of water and the total solution is evaporated in vacuo. The liquid residue thus obtained is suspended in a mixture of 100 ml each 25% sodium hydroxide and 90% ethanol and heated on water bath for 1 hour. The mixture is cooled and the product extracted with ether and ethyl acetate. After drying the organic layers and solvent removal, the residue, 13.8 g, is chromatographed on 450 g of neutral alumina (grade II). Elution with chloroformmethanol (95:5%) gives 5.8 g of the desired tetrol as a colorless foam.

A suspension of 5.8 g (0.22 moles) of noncrystalline tetrol in 200 ml of acetic anhydride is cooled in a dry ice-acetone bath while 3.36 g of 70% $HClO_4$ (0.0234 moles) is added. The resulting pink solution is stored at −20° for 16 hours. The solution is cooled in a dry ice-acetone bath while 125 ml of dry methanol is added dropwise. The solution is then basified with cold concentrated aqueous ammonia and extracted with chloroform. The organic layer is dried and evaporated in vacuo to give 8.2 g of semisolid which is filtered to give 4.3 g of the acetate. A sample recrystallized from ethyl acetate-hexane has mp 103°–105°.

EXAMPLE 35

2,3:4a,8a-trans-Decahydro-1-[(1-methyl-3-pyrrolidinyl)-methyl]-2,3,4a,8a-naphthalenetetrol To a suspension of 0.5 moles of sodium amide in 500 ml of liquid ammonia is added 48 g (0.26 moles, 80% purity) 1,2,3,4,5,8-hexahydronaphthalene in 125 ml of ether. After 15 minutes of stirring, the mixture is treated portionwise with 35.5 g (0.26 moles) of n-methyl-(2-chloromethyl)pyrrolidine in 125 ml of ether. After addition is completed stirring is continued for 1 hour, before the addition of 500 ml of ether and quenching with solid ammonium chloride as rapidly as possible. After ammonia has evaporated solids are removed by filtration and solvents removed in vacuo to give 59 g of liquid. This liquid on acid and base extraction gives 35 g of oil which is distilled at the oil pump to give 28° of monoamino alkyldiene bp 105°–106°/0.05 mm and 5 g of bis-alkylation product, bp 155°–163°/0.05 mm.

An amount of 23.1 g (0.1 mol) of the monoalkylated diene is dissolved in 200 ml of cold 88% formic acid and treated over a period of 15 minutes with 24.1 ml (0.27 moles, 2.71 equivalents) of 30% hydrogen peroxide. The solution is permitted to warm from 20° to 35° during this addition and 35° to 48° in the next 5 minutes. A cold bath is applied for 15 minutes to maintain the temperature between 48°–42° C, in the next 45 minutes, the solution is left stirring overnight at room temperature. The solution is diluted with 200 ml of water, and the solvents are evaporated in vacuo. The liquid residue is then taken up in 300 ml of ethanol and hydrolyzed by the addition of 125 ml of 25% sodium hydroxide solution. The temperature is allowed to rise to 65° and stirring continued for one hour. The mixture is cooled and the product extracted into ether and ethyl acetate. After drying the organic layers and solvent removal the residue 17.9 g is chromatographed on 500 g of neutral alumina (grade II). Elution with chloroform-methanol (95:5%) gives 8.2 g of oil which on trituration gives a solid 6 g, mp 172°–174°. A sample recrystallized from ethyl acetate has mp 176°–178° C.

EXAMPLE 35a 2,3:4a,8a-trans-Decahydro-1-[(1-methyl-3-pyrrolidinyl)methyl]-2,3,4a,8a-naphthalenetetrol, tetraacetate ester, hydrochloride A 2.99 g sample of the product of example 35 (0.01 moles) in 75 ml of acetic anhydride and 5 ml of acetic acid is cooled to −78° C and treated with 1.2 g (0.012 moles) of 70% perchloric acid. The slurry is allowed to warm to −20° C overnight, then with carbon-dioxide acetone coupling, the resulting clear solution is treated with 50 ml of dry methanol over 30 minutes. The cold mixture is added to an ice-cooled mixture of chloroform and concentrated aqueous ammonia, the layers separated, and the aqueous extracted again with chloroform. The organics are dried (sodium sulfate and then magnesium sulfate) and evaporated to give 3.6 g of tetraacetate as an oil. A 1.6 g of the sample is dissolved in 50 ml of anhydrous ether and dry hydrochloric acid in isopropanol-ether is added until the solution is acidic to pH paper. The solid is filtered and recrystallization from ethyl acetate-hexane affords the analytical sample 0.8 g, mp 85°–87°.

EXAMPLE 36

2,3:2,4a:4a,8a-trans-1-[3-(Dimethylamino)propyl]-decahydro-2,3,4a,8a-naphthalenetetrol, tetraacetate ester To a suspension of 1.0 mole of sodium amide in 1 liter liquid ammonia is added 75 g (0.5 moles, 90% purity) 1,2,3,4,-5,8-hexahydronaphthalene in 125 ml of ether. After 15 minutes of stirring, the mixture is treated portionwise with 62 g (0.5 moles) of dimethylaminopropyl chloride in 125 ml of ether. After addition is completed stirring is continued 1 hour, before the addition of 500 ml of ether and quenching with solid ammonium chloride as rapidly as possible. After ammonia has evaporated solids are removed by filtration and solvents removed in vacuo to give 71 g of liquid. This liquid on acid and base extraction gives 60 g of oil which is distilled at the oil pump to give 48 g of monoaminoalkyl diene bp 87°–90°/0.05 mm and 6 g of bis-alkylation product, bp 90°–100°/0.05 mm.

An amount of 32.90 g (0.15 moles) of 5-[3-(dimethylamino)propyl]-1,2,3,4,5,8-hexahydronaphthalene is dissolved in 250 ml of cold 88% formic acid, and treated over a period of 15 minutes with 39 ml of 30% hydrogen peroxide (0.41 moles). The temperature rises from 20° to 48° during the next 20 minutes. A cold bath is applied as needed to maintain temperature between 48°–42° C. The both is removed and the temperature drops from 42° to 30° in the next 60 minutes, the solution is left stirring overnight at room temperature. The solution is diluted with 250 ml of water and total solution is evaporated in vacuo. The liquid residue is suspended in a mixture of 400 ml each 25% sodium hydroxide and 90% ethanol and heated on water bath for 1 hour. The mixture is cooled and the product extracted with ether and ethyl acetate. After drying the organic layers and solvent removal the residue, 40 g, is chromatographed on 1 kg of neutral alumina (grade II). Elution with chloroform-methanol (95:5%) gives 17 g of colorless foam, homogenus by tlc to be the desired tetrol.

A suspension of 5.74 g (0.02 moles) of 4-[3-(dimethylamino)propyl]decahydro-2,3,4a,8a-naphthalenetetrol in 150 ml of acetic anhydride is cooled in a dry ice-acetone bath while 3.014 g of 70% HClO$_4$ (0.022 moles) is added. The resulting pink solution is stored at −20° for 16 hours. The solution is cooled in a dry ice-acetone bath while 100 ml of methanol is added dropwise over 45 minutes. The solution is then basified with cold concentrated aqueous ammonia and extracted with chloroform. The chloroform layer is washed with saturated sodium chloride solution dried on magnesium sulfate and evaporated in vacuo, to give 8.2 g of an oil, which on trituration gives a solid melting point 112°–114° (3.9 g). A sample recrystallized from ethyl acetate-hexane has mp 117° C.

EXAMPLE 37

| Preparation of capsule formulation | |
|---|---|
| Ingredient | Milligrams per Capsule |
| 3a, 7a-trans-5,6-trans-Hexahydro-4-(3-piperidinopropyl)-3a,5,6,7a-indantetrol, tetraacetate ester | 400 |
| Starch | 80 |
| Magnesium stearate | 5 |

The active ingredient, starch and magnesium stearate are blended together. The mixture is used to fill hard shell capsules of a suitable size at a fill weight of 485 milligrams per capsule.

EXAMPLE 38

| Preparation of tablet formulation | |
|---|---|
| Ingredient | Milligrams per Tablet |
| 3a,7a:5,6-trans-4-[3-(Dimethylamino)-propyl]-hexahydro-1H-indene-3A,5,6,7A-tetrol, tetraacetate ester | 100 |
| Lactose | 200 |
| Corn starch (for mix) | 50 |
| Corn starch (for paste) | 50 |
| Magnesium stearate | 6 |

The active ingredient, lactose and corn starch (for mix) are blended together. The corn starch (for paste) is suspended in water at a ratio of 10 grams of corn starch per 80 milliliters of water and heated with stirring to form a paste. This paste is then used to granulate the mixed powders. The wet granules are passed through a No. 8 screen and dried at 120° F. The dry granules are passed through a No. 16 screen. The mixture is lubricated with magnesium stearate and compressed into tablets in a suitable tableting machine. Each tablet contains 100 milligrams of active ingredient.

EXAMPLE 39

| Preparation of oral syrup formulation | |
|---|---|
| Ingredient | Amount |
| 1,2:4,5-trans-3-[3-(Dimethylamino)propyl]-1,2-dimethyl-1,2,4,5-cyclohexanetetrol, tetraacetate ester | 500 mg. |
| Sorbitol solution (70% N.F.) | 40 ml. |
| Sodium benzoate | 150 mg. |
| Sucaryl | 90 mg. |
| Saccharin | 10 mg. |
| Red Dye (F.D. & Co. No. 2) | 10 mg. |

| -continued | |
|---|---|
| Preparation of oral syrup formulation | |
| Ingredient | Amount |
| Cherry flavor | 50 mg. |
| Distilled water qs to | 100 ml. |

The sorbitol solution is added to 40 milliliters of distilled water and the active ingredient is suspended therein. The sucaryl, saccharin, sodium benzoate, flavor and dye are added and dissolved in the above solution. The volume is adjusted to 100 milliliters with distilled water.

Other ingredients may replace those listed in the above formulation. For example, a suspending agent such as bentonite magma, tragacanth, carboxymethylcellulose, or methylcellulose may be used. Phosphates, citrates or tartrates may be added as buffers. Preservatives may include the parabens, sorbic acid and the like and other flavors and dyes may be used in place of those listed above.

What is claimed is:
1. A compound of the formula

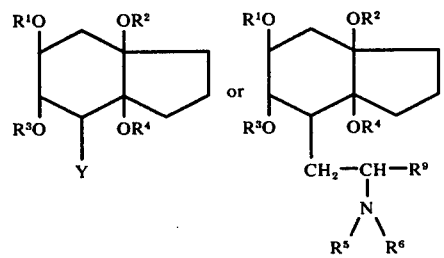

wherein
Y is a radical of the formula

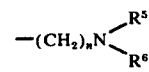

or of the formula

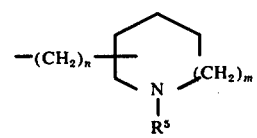

wherein $(CH_2)_n$ is a straight or branched chain alkyl radical, n is 1-6, $m$ is 0 or 1 and $R^5$ and $R^6$ are the same or different and are hydrogen, alkyl of from 1 to 3 carbons, benzyl, or $R^5$ and $R^6$ together with the nitrogen to which they are attached are pyrrolidino, piperidino or N'-alkyl piperazino wherein the alkyl radical has from 1 to 3 carbons; $R^1$, $R^2$, $R^3$ or $R^4$ are the same or different and are hydrogen; alkyl of from 1 to 4 carbons, trifluoromethyl; alkanoyl of from 1 to 4 carbons; haloalkanoyl of from 1 to 4 carbons; alkoxycarbonyl of the formula

wherein R is an alkyl radical of 1 to 4 carbons; alkoxyalkyl wherein the alkoxy group has 1 to 3 carbons and the alkyl has 1 to 3 carbons; aminoalkanoyl of the formula

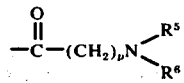

wherein $R^5$ and $R^6$ are as previously defined and $p$ is 0–3; 2-, 3-, or 4-pyridylcarbonyl; phenyl; monosubstituted phenyl wherein the substituent is alkyl of from 1 to 4 carbons, alkoxy of from 1 to 4 carbons, hydroxy, nitro, amino, or dialkylamino wherein each alkyl has from 1 to 4 carbons; alkenoyl of from 3 to 4 carbons; or aroyl of the formula

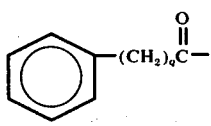

wherein $q$ is 0–3;

and $R^9$ is alkyl of from 1 to 4 carbons, phenyl, hydrogen, alkyl of 1 to 4 carbons substituted by phenyl or phenoxy or by a substituted phenyl or phenoxy wherein the substituent is halogen, amino, alkyl of 1 to 4 carbons, alkoxy of 1 to 4 carbons or dialkylamino wherein each alkyl is from 1 to 4 carbons.

2. A compound of claim 1 wherein $R^1$, $R^2$, $R^3$ and $R^4$ are hydrogen or alkanoyl of from 1 to 4 carbons.

3. A compound of claim 2 wherein $R^1$, $R^2$, $R^3$ and $R^4$ are acetyl.

4. The compound as defined in claim 1 having the name 3a,7a-trans-5,6-trans-hexahydro-4-(3-piperidinopropyl)-3a,5,6,7a-indantetrol.

5. The compound is defined in claim 1 having the name 3a,7a-trans-5,6-trans-hexahydro-4-(3-piperidinopropyl)-3a,5,6,7a-indantetrol, tetraacetate ester.

* * * * *

UNITED STATES PATENT AND TRADEMARK OFFICE
CERTIFICATE OF CORRECTION

PATENT NO. : 4,022,788

DATED : May 10, 1977

INVENTOR(S) : Frederic Peter Hauck et al

It is certified that error appears in the above-identified patent and that said Letters Patent are hereby corrected as shown below:

Column 1, lines 41-48, the formula should read -- $-(CH_2)_n N\genfrac{}{}{0pt}{}{R^5}{R^6}$ --.

Column 1, first formula "$LR^8$" should read --$R^8$--.
Column 1, line 64, "piperazin-" should read --piperazino--.
Column 2, line 54, "or" should read --in--.
Column 2, last formula, "$LR^8$" should read --$R^8$--.

Column 12, line 55, "both" should read --bath--.
Column 13, Example 38, second line of first ingredient, "3A,5,6,7A" should read --3a,5,6,7a--.

Signed and Sealed this twenty-third Day of August 1977

[SEAL]

Attest:

RUTH C. MASON
*Attesting Officer*

C. MARSHALL DANN
*Commissioner of Patents and Trademarks*